United States Patent [19]

Nagai

[11] 4,446,149
[45] May 1, 1984

[54] MEDICINE FOR TREATMENT OF CERVICAL EROSION

[76] Inventor: Kineshiro Nagai, No. 22-2, Yoyogi 4-Chome, Shibuya-Ku, Tokyo, Japan

[21] Appl. No.: 447,650

[22] Filed: Dec. 7, 1982

[30] Foreign Application Priority Data

Dec. 14, 1981 [JP] Japan ................................ 56-201345

[51] Int. Cl.³ ........................................... A61K 31/415
[52] U.S. Cl. ......................... 424/273 R; 424/DIG. 15
[58] Field of Search ..................... 424/273 R, DIG. 15

[56] References Cited

U.S. PATENT DOCUMENTS 4,359,416 11/1982 Vinick .................................. 548/344

FOREIGN PATENT DOCUMENTS 2758787 7/1979 Fed. Rep. of Germany ... 424/DIG. 15
2759166 7/1979 Fed. Rep. of Germany ... 424/DIG. 15

Primary Examiner—Jerome D. Goldberg
Assistant Examiner—Freda Abramson
Attorney, Agent, or Firm—McDermott, Will & Emery

[57] ABSTRACT

L-carnosine having the chemical formula

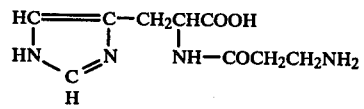

or physiologically acceptable salts thereof are specifically effective as a medicine for treatment of cervical erosion (erosio portionis).

5 Claims, No Drawings

MEDICINE FOR TREATMENT OF CERVICAL EROSION

BACKGROUND OF THE INVENTION

1. Field of the Invention

This invention relates to a medicine for treatment of cervical erosion (erosio portionis). More particularly, this invention relates to a medicine for treatment of cervical erosion comprising L-carnosine or physiologically acceptable salts thereof as an effective ingredient.

2. Brief Description of the Prior Art

Cervical erosion refers to an inflamed condition in which the squamous flat epithelia that usually cover the uterine cervix are replaced by columnar epithelia of a fresh scarlet color. Pathohistologically, an erosion refers to a state where epithelia desquamates and what we mean by cervical erosion is not the same as this genuine erosion but may be called a pseudo-erosion.

In terms of macroscopic findings, cervical erosion is generally classified into the following three categories: (1) where the boundary between the adjacent tissues and the eroded part covered by columnar epithelia is relatively obscure, the surface being devoid of convexities and concavities; a simple erosion which has a fresh scarlet color, (2) where the surface has assumed a papillar form through the proliferation of columnar epithelia representing a papillar-like erosion attended by a fresh scarlet color full of convexities and concavities and (3) where, because of the closure of the secretory glands, the secretion gathers on the surface of the uterine cervix, leading to the production of small cysts on the eroded surface. It is the practice to classify erosions into these three categories, but it is maintained that no special distinction is necessary from the viewpoint of treatment.

As for the genesis of cervical erosion, many theories have been proposed to date. R. Meyer (1910) said that inflammation of the uterine cervix brings about an increased secretion of alkaline substance and, because of this secretion, flat epithelia of the uterine cervix tend to fall off, resulting in a genuine erosion. Subsequently, columnar epithelia come to proliferate to cover that portion devoid of epithelia thus producing a pseudo-erosion. According to Kaufmann et al. (1958), the presence of genuine erosion is not necessary for the emergence of columnar epithelia on the surface of the uterine cervix and when a woman attains sexual maturity the uterine cervix is caused to enlarge in volume by estrogen and because of this, the inside of the uterine cervix comes to be reversed and an erosion will set in. Meyer's theory is refuted by many modern investigators but, at any rate, no satisfactory explanation regarding the genesis of cervical erosion has yet been put forth.

Simple cervical erosion is free from any particular grave symptoms but the eroded surface is susceptible to bacterial infection and inflammation of the uterine cervix is often observed as a complication. Subjective symptoms include leucorrhea, vaginal bleeding through sexual contact, abdominal pain and lumbago.

For treatment of cervical erosion, such antibiotics and anti-inflammatory medicines as AZAROMYCIN-F (Sankyo Co., Ltd.), TRICHOMYCIN (Fujisawa Pharmaceutical Co., Ltd.), SOLCOSERYL (Tobishi Pharmaceutical Co., Ltd.), PENTAMYCIN-K (Nikken Chemical Co., Ltd.) have been employed. Although these medicines have indirect effects in treatment of cervical erosion, they fall far short of a radical cure. As further measures, recourse is had to the local administration of $AgNO_3$ solution, electric cauterization, high frequency electric coagulation and cauterization with laser beam, but the effectiveness of these measures in inducing regeneration of epithelia is far from being satisfactory. As a final measure, since there is no definite cure employing either medicines or physical therapy, surgery is used. That is to say, the uterine cervix including the eroded portion is surgically excised in a conical manner. This conical excision cannot, however, be applied to light and heavy cases of cervical erosion alike. In young women, in particular, there is a fear that infertility may result and, for this reason, this surgical operation is not widely practised. Therefore, a radical treatment of the disease by some kind of medicine would be best but at present no medicine capable of providing such treatment is available.

BRIEF SUMMARY OF THE INVENTION

The principal object of the present invention is to provide an effective medicine for treatment of cervical erosion, said medicine comprising L-carnosine or physiologically acceptable salts thereof.

The inventor of the present invention has, over many years, conducted studies on the physiological significance and pharmacological utility of L-carnosine, which is a dipeptide contained in living organisms. In this connection, the inventor discovered the fact that L-carnosine and its physiologically acceptable salts have an excellent effect in the treatment of cervical erosion.

DETAILED DESCRIPTION OF THE INVENTION

The effective ingredient used in the present medicine, L-carnosine, i.e. β-alanyl-L-histidine, was discovered in a meat extract by Gulewitch et al. in 1900. A dipeptide consisting of L-histidine and β-alanine, L-carnosine is a white crystalline powder easily soluble in water and tasteless and odorless.

m.p. 250° C. (decomp.), $[\alpha]_D^{20} = +20.0°$ ($H_2O$)

It is represented by the following chemical formula.

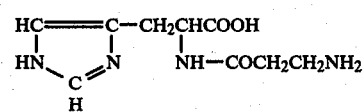

The pH value of its aqueous solution is 8.0–8.5. Since its discovery, many investigators have studied the physiological significance and pharmacological activities of L-carnosine, but they did not find any pronounced effect on any bodily organ and its physiological significance has remained unexplained to the date. L-carnosine is a substance which is chiefly present in the skeletal muscle of vrious mammals in an amount of about 0.1–0.3% and it is taken into the human body from meat foods and is a source of supply of an essential amino acid, L-histidine. It is also biosynthesized from L-histidine and β-alanine. L-carnosine thus taken into the body is decomposed, with the aid of carnosinase, into L-histidine and β-alanine, which serve as nutritional sources. At the same time, part of these are resynthesized as L-carnosine. There is an intermediate substance in the biosynthesis of L-carnosine known as β-alanyl-1-methyl-histidine (anserine).

As stated above, the fact that L-carnosine is a safe, food-like substance which, after intake, it is decomposed by carnosinase existing in various organs makes it entirely different from the majority of commercially available medicines that are metabolized in the liver and thus put a burden on the liver function.

The method of synthesizing L-carnosine is publicly known (Journal of Biological Chemistry, 108, 753, 1935). L-carnosine is obtained by converting carbobenzoxy β-alanine to its chloride with phosphorus pentachloride, esterifying the chloride to its methyl ester by the use of methanol, converting to the azide via hydroazide, coupling the azide with L-histidine methyl ester and finally removing carbobenzoxy radical by catalytic reduction. The medicines of the present invention also include medicines derived from physiologically acceptable salts of L-carnosine. As the salts of L-carnosine, salts based on carboxyl radicals and addition salts with physiologically acceptable acids based on amino radicals may be mentioned. Salts based on both carboxylic and amino radicals may also be mentioned. Salts based on carboxyl radical include metallic salts such as sodium, potassium, calcium, magnesium, zinc and aluminum salts, ammonium salts and substituted ammonium salts such as trialkylamine salts, e.g. triethylamine salt. Those based on amino radical include salts with inorganic or organic acids such as hydrochloric, sulfuric, phosphoric, acetic, propionic, lactic, tartaric, citric, succinic, maleic, benzenesulfonic and toluenesulfonic acids. These salts can be prepared by the well-known method, i.e. by the reaction of L-carnosine in its free form with the selected acid or base in stoichiometrical amount.

The following paragraph deals with the toxicity of L-carnosine.

Acute toxicity of L-carnosine 10 mice in 1 group were subjected to various dosages of L-carnosine peritoneally and orally for examination of acute toxicity 5 hours after its administration. $LD_{50}$ was computed by the Van der Waerden method based on the number of dead mice after 72 hours. In the examination, L-carnosine was diluted with a physiological saline so that its administration concentration would be 0.1–0.3 ml/10 g.

After about 30 minutes of peritoneal administration of 15,000 mg/kg ($LD_{100}$) of L-carnosine there occured a reduction in spontaneous movement accompanied by an irregular or decreased number of respirations but there were observed no frontal or escape reflexes, and an intermittent raising of the tails and clonospasm were seen in as many as half of the experimental animals. When the symptoms further advanced, the animals repeated horizontal rollings and upon contact stimulation the reflex became hyperreactive with an attendant spasm, leading to ultimate death brought about by a entasia. Half of the experimental animals died after 1 hour and 30 minutes, 80% of them after 2 hours, and after 5 hours all of the experimental animals died. An oral administration of 15,000 mg/kg L-carnosine did not show any appreciable effect in this respect but 1 mouse out of 10 died after 12 hours.

TABLE 1

| Dosage | $LD_{50}$ of L-carnosine $LD_{50}$ at 95% level of confidence mg/kg |
|---|---|
| Peritoneal | 9,087 (8,320–9,925) |
| Oral | >14,930 (the minimum lethal dose) |

The above table is based on acute toxicity test of L-carnosine on dd strain male mice (75-hour value) and therefore, it can be said that it is a chemical compound of quite low toxicity.

In administering the medicine of this invention for a given disease it makes no difference in what form it is administered. As convenient, it can be administered as ointment, suppository, powder, injection fluid or troche and anal administration is also acceptable. The aforesaid forms are used singly or in combination, depending on the symptoms of the patient.

The ointment is produced according to an known procedure by mixing fine powder of L-carnosine in an amount resulting in e.g. 5% or 10% concentration in the finished ointment with an ointment base, such as bleached beeswax, whale wax, anhydrous lanoline, white petrolatum, higher alcohol, macrogols or Plasti Base (hydrocarbon gel ointment base manufactured by Taisho Pharmaceutical Co., Ltd.), hydrophilic ointment, water absorbing ointment or mixtures thereof. If necessary, oils such as sesame oil, peanut oil and olive oil, resin material, glycerine, propyleneglycol, surfactant, germicide, fungicide, antioxidant etc., are further added and the mixture thus obtained is kneaded to produce L-carnosine ointment of uniform quality.

The L-carnosine suppository is made in almost the same manner as the ointment. For instance, the suppository is prepared by adding antiseptics and L-carnosine into a melted suppository base, mixing thoroughly, casting the mixture into a mold and removing it from the mold when it has solidified.

In preparing its powder form, synthesized L-carnosine is pulverized and sieved with a 200-mesh sieve. Subsequently, it is placed in a glass vessel and sterilized by heating for several hours at a temperature of about 120° C.

Since L-carnosine is readily soluble in water, there is no difficulty in preparing 3%, 5% or 10% aqueous solutions of L-carnosine under aseptic conditions. The solution thus prepared is put into ampoules under a current of an inert gas and is injected using an ordinary syringe. Alternatively, it is possible to make use of freeze dried L-carnosine placed in ampoules or vials under aseptic processing and to use it for injectional purposes by making 3%, 5% or 10% solution by the addition of sterilized distilled water just before the injection.

L-carnosine is administered in various manners such as by direct insertion of a suppository into the vagina, intervaginal application of paste or ointment, intervaginal spray of powder or a local injection into the affected place. The dosage naturally depends largely on the method of administration, the form of the L-carnosine preparation and the symptoms of the patient. The following list gives typical forms of preparation, dosages and methods of administration.

| Form of Preparation | Dosage and Administration |
|---|---|
| Suppository | A suppository containing 200 mg L-carnosine is inserted into the |

-continued

| Form of Preparation | Dosage and Administration |
| --- | --- |
| Ointment | vagina at one time.<br>An ointment of 5% L-carnosine is used in the vagina 2 g at one time. |
| Injection solution | An injection of 5% L-carnosine solution into the vagina locally in the amount of 0.1–1.0 ml at one time. |

Since these are only rough standards and, as stated above, L-carnosine is a very safe chemical compound, the dosage can be increased or decreased freely depending on the symptoms of the patient.

L-carnosine preparations are given as follows:

EXAMPLE 1 (Suppository)

According to the following prescription, a suppository was prepared using Hosco S-55 (suppository base manufactured by Maruishi Pharmaceutical Co., Ltd.) as a suppository base and synthesized L-carnosine.

| Prescription | |
| --- | --- |
| L-carnosine | 0.2 g |
| p-Oxyethylbenzoate | 0.00085 g |
| Hosco S-55 | 1.5 g |
| | (per suppository) |

In this preparation, L-carnosine and p-oxyethylbenzoate were sieved using a 200 mesh sieve and were added little by little into the Hosco S-55 melted at 50° C. so as to obtain a uniform mixture. The mixture was poured into a mold at 38° C., and after cooling at room temperature, it was frozen in a freezer. The product thus obtained was removed from the mold and wrapped up in paraffin paper.

EXAMPLE 2 (Ointment)

According to the following prescription, 5% ointment was prepared using a hydrocarbon gel ointment base and synthesized L-carnosine.

| Prescription | |
| --- | --- |
| L-carnosine | 5 g |
| Hydrocarbon gel ointment base | 95 g |
| | 100 g |

EXAMPLE 3 (Powder)

Synthesized L-carnosine crystals were pulverized with an electric mortar and were subsequently sieved using a 200 mesh sieve. The obtained fine powder was placed in a glass vessel and was sterilized for 3 hours at 121° C.

EXAMPLE 4 (Injection Solution)

Under aseptic conditions, a mixture of L-carnosine powder and its hydrochloride powder in equal amounts was dissolved into sterilized distilled water to prepare 3%, 5% and 10% solutions, and the solutions were put into ampoules.

The following cases are illustrative examples in which the medicine of the present invention was administered to patients diagnosed as suffering cervical erosion. In evaluating the effect of L-carnosine, the following criteria were adopted.

Non effective: Cases in which no improvement occured.

Effective: Cases in which there was no leucorrhea bleeding in the eroded part of the vagina, the entire region being restored to the normal state.

Highly effective: Cases in which macroscopic inspection and pathohistodiagnosis confirmed the patient to be completely cured. Class 1 in cytologic findings. There was no leucorrea bleeding and the degree of vaginal cleanliness was normal with no other complications.

The expression of the cytologic findings is in accordance with the following classification.

Class I: Absence of atypical or abnormal cells

Class II: Atypical cytology but no evidence of malignancy

Class III: Cytologic suggestive of, but not conclusive for malignancy (Class III is further divided into Class $III_a$ and Class $III_b$. $III_a$ is close to benignancy and $III_b$ is close to malignancy.)

The suppository used in these treatment reports contained 200 mg of L-carnosine per suppository (1.7 g). The ointment contained 5% of L-carnosine.

Case No. 1

♀ 38 years old

Diagnosis:
Cervical erosion
Malignant neoplasm was not found by pathohistodiagnosis.
Cytologic findings:
Vaginal part: Class $III_a$
Cervical part: Class $III_a$ Anamnesis:
The patient came for consultation with a heavy complaint of leucorrhea and was diagnosed as suffering cervical erosion. Bacteriological test revealed no noteworthy abnormality, Candida being (−) and Trichomonas being (−). But one year later the patient came to the clinic again complaining that her leucorrhea had become worse. Even then there were no abnormal bacteriological test findings. At the time of the third consultation three months later, her leucorrhea was (++) with occasional bleeding. The cytologic findings confirmed the patient to be in the vaginal class IIIa and cervical class IIIa. In the pathohistodiagnois, there was no evidence of malignancy.

Dosage of L-carnosine:
Medication with L-carnosine was started from the third visit and continued for three months and a half. During the period, L-carnosine suppositories were used 19 times with 2 suppositories being administered each time. 200 mg×2×19

Combination with other medicine:
None.

Treatment history of the case:
During the above treatment period, L-carnosine suppositories were administered at intervals of three to seven days. A clinical test after the third administration (the total amount of L-carnosine used was 200 mg×2×3) confirmed the patient's condition to be considerably improved. The cytologic findings revealed vvaginal class I and cervical class IIIa. After 17th treatment, the disease was confirmed to have been cured as determined by macroscopic inspection. The findings of a corporeal test were also found to be normal. After the 19th treatment with two further additional medications, the result of a cytologic findings confirmed the patient to have been completely cured of her cervical erosion and to be of vaginal class I and cervical class I.

Side effects:
 There were observed no adverse side effects either locally or systemically.

Prognosis:
 Results of tests carried out five months after the disease was cured did not reveal the presence of erosion.

Effect:
 Highly effective.

Case No. 2
♀ 40 years old

Diagnosis:
 Cervical erosion
 Malignant neoplasm was not found by pathohistodiagnosis.
 Cytologic findings
  Vaginal part: Class $III_b$
  Cervical part: Class $III_b$ Anamnesis:
 The patient came to consult a physician with a complaint of bleeding after her menstrual period. The cytologic findings revealed vaginal class $III_b$ and cervical class $III_a$. The cytologic findings two weeks later revealed vaginal class $III_b$ and cervical class $III_b$. There was no evidence of malignancy.

Dosage of L-carnosine:
 For three months from the day of the second diagnosis, 2 g of L-carnosine ointment applied to a tampon was used 11 times at intervals of about seven days. 2 g×0.05×11

Combination with other medicine:
 None.

Treatment history of the case:
 After the 11th treatment, the disease was confirmed to have been cured as determined by macroscopic inspection. At that time, the cytologic findings revealed vaginal class I and cervical class I. Erosion was confirmed to be completely cured by pathohistodiagnosis.

Side effects:
 There were observed no adverse side effects either locally or systemically.

Prognosis:
 A macroscopic inspection, about one year after the disease was cured, revealed no abnormal findings.

Effect:
 Highly effective.

Case No. 3
♀ 36 years old

Diagnosis:
 Cervical erosion and hysteromyoma
 Malignant neoplasm was not found by pathohistodiagnosis.
 Cytologic findings
  Vaginal part: Class II
  Cervical part: Class II Anamnesis:
 The patient came for consultation with a complaint of blood coagulation in connection with her menses and was diagnosed as a case of hysteromyoma. About four years later, on her second visit, cervical erosion was discovered. Cytologic findings showed vaginal class II and cervical class I. Findings in tests about two years later were vaginal class II and cervical class II.

Dosage of L-carnosine:
 For four months from about six months after the third visit, L-carnosine suppositories were administered 10 times to the patient at intervals of ten to fourteen days. Two tables were used at a time. 200 mg×2×10

Combination with other medicine:
 None.

Treatment history of the case:
 A macroscopic inspection after the third treatment confirmed a remission of cervical erosion as well as leucorrhea. After the tenth treatment, erosion was confirmed to be cured by a macroscopic inspection. In terms of cytologic findings, the organs in question improved to vaginal class I and cervical class I. A pathohistodiagnosis also confirmed the patient to be completely cured.

Side effects:
 There were observed no adverse side effects either locally or systemically.

Prognosis:
 An examination after about four months of complete cure confirmed that there was no evidence of replace of the cervical erosion. No abnormal state was observed in the vaginal and cervical region under a macroscopic inspection.

Effect:
 Highly effective.

Case No. 4
♀ 35 years old

Diagnosis:
 Cervical erosion
 Malignant neoplasm was not found by pathohistodiagnosis.
 Cytologic findings
  Vaginal part: Class II
  Cervical part: Class II Anamnesis:
 The patient came for consultation with a complaint of leucorrhea and bleeding upon sexual contact. Cytologic findings on the day of the first diagnosis revealed vaginal class II and cervical class II. In terms of the pathohistodiagnosis, there was no evidence of malignancy.

Dosage of L-carnosine:
 For sixty-five days from the day of the first diagnosis, L-carnosine suppositories were used 10 times at intervals of about seven days with one suppository administered each time. 200 mg×10

Combination with other medicine:
 None.

Treatment history of the case:
 A macroscopic inspection after the tenth treatment did not reveal any abnormal findings. There was no complication and the tissue image was normal.

Side effects:
 There were observed no adverse side effects either locally or systemically.

Prognosis:
 An examination one year after complete cure confirmed that there was no evidence of relapse of the cervical erosion. No abnormal state was observed under a macroscopic inspection.

Effect:
  Highly effective.

Case No. 5
♀ 32 years old

Diagnosis:
  Cervical erosion
  Malignant neoplasm was not found by pathohistodiagnosis.
  Cytologic findings
    Vaginal part: Class II
    Cervical part: Class II
Anamnesis:
  The patient came for consultation with a complaint of leucorrhea and bleeding upon sexual contact. Cytologic findings on the day of the first diagnosis revealed vaginal class II and cervical class II. In terms of the pathohistodiagnosis, there was no evidence of malignancy.
Dosage of L-carnosine:
  For about four months and a half from the day of the first diagnosis, L-carnosine suppositories were administered 5 times to the patient at intervals of about four weeks. One suppository was used each time. 200 mg×5
Combination with other medicine:
  None.
Treatment history of the case:
  After the fifth treatment, both macroscopic inspection and pathohistodiagnosis confirmed the complaint to be completely cured.
Side effects:
  There were observed no adverse side effects either locally or systemically.
Prognosis:
  A macroscopical inspection about nine months after the disease was cured did not reveal any abnormal findings.
Effect:
  Highly effective.

Case No. 6
♀ 35 years old

Diagnosis:
  Cervical erosion and hysteromyoma
  Malignant neoplasm was not found by pathohistodiagnosis.
  Cytologic findings
    Vaginal part: Class II
    Cervical part: Class II
Anamnesis:
  Hysteromyoma was discovered about four years earlier. About one year earlier, the patient came for consultation with a complaint of leucorrhea and bleeding upon sexual contact. As a result, she was diagnosed as a case of cervical erosion.
Dosage of L-carnosine:
  For about four weeks from the diagnosis as cervical erosion, L-carnosine suppositories were administered eight times, twice a week. One suppository was used each time. 200 mg×8
Combination with other medicine:
  None.
Treatment history of the case:
  On the seventh day from the starting of the treatment during which two L-carnosine suppositories were administered, evidence of leucorrhea had disappeared and the degree of vaginal cleanliness was much improved. The result of a macroscopical inspection confirmed the erosion to be cured on the thirtieth day. Pathohistodiagnosis revealed no abnormal findings.
Side effects:
  There were observed no adverse side effects either locally or systemically.
Prognosis:
  About nine months after the cure of the disease there was found no relapse of the cervical erosion.
Effect:
  Highly effective.

Case No. 7
♀ 36 years old

Diagnosis:
  Cervical erosion and hysteromyoma
  Malignant neoplasm was not found by pathohistodiagnosis.
  Cytologic findings
    Vaginal part: Class II
    Cervical part: Class II
Anamnesis:
  Hysteromyoma was discovered about six years earlier. About one year earlier, the patient came for consultation with a complaint of leucorrhea and bleeding upon sexual contact. She was diagnosed as a case of the cervical erosion.
Dosage of L-carnosine:
  For about two months from the day of the diagnosis as cervical erosion, L-carnosine suppositories were administered eight times, once per week. One suppository was used each time. 200 mg×8
Combination with other medicine:
  None.
Treatment history of the case:
  After two weeks during which two suppositories were administered, the patient did not complain of subjective symptoms of either leucorrhea or bleeding upon sexual contact. Two months later, a macroscopic inspection together with cytologic findings and pathohistodiagnosis revealed no abnormal findings, the final verdict being a complete cure.
Side effects:
  There were observed no adverse side effects either locally or systemically.
Prognosis:
  A macroscopic inspection about nine months after the cure revealed no abnormal findings.
Effect:
  Highly effective.

Case No. 8
♀ 32 years old

Diagnosis:
  Cervical erosion
  Malignant neoplasm was not found by pathohistodiagnosis.
  Cytologic findings
    Vaginal part: Class II
    Cervical part: Class II
Anamnesis:
  The patient came for consultation with a complaint of leucorrhea about one year earlier and was diagnosed as a case of cervical erosion. She said that she had been aware of subjective symptoms for two years.
Dosage of L-carnosine:

For about two months and a half from the day of the first diagnosis as cervical erosion, L-carnosine suppositories were used 9 times at intervals of one week with one suppository administered each time. 200 mg×9

Combination with other medicine:

None.

Treatment history of the case:

After two weeks during which two suppositories were administered, evidence of leucorrhea had disappeared and degree of vaginal cleanliness was much improved. After the ninth treatment, i.e. about two months and a half after the day of the first diagnosis, a macroscopic inspection together with cytologic findings and pathohistodiagnosis revealed no abnormal findings, the final verdict being a complete cure.

Side effects:

There were observed no adverse side effects either locally or systemically.

Prognosis:

A macroscopic inspection about five months after the disease was cured revealed no abnormal findings.

Effect:

Highly effective.

Summary of these treated cases

Treatment of cervical erosion of vaginal and cervical class II–III$_b$ by cytologic findings was become possible by the administration of 5% L-carnosine ointment or suppository containing 200 mg of L-carnosine. These diseases have been considered almost impossible of cure by either pharmacological or physicotherapy means.

What is claimed is:

1. A method of treating cervical erosion in a human female suffering therefrom comprising the step of administering a preparation containing L-carnosine or physiologically acceptable salts thereof in an effective amount for treating cervical erosion in said human female.

2. The method of treating cervical erosion according to claim 1, wherein said preparation is administered in the form of a suppository.

3. The method of treating cervical erosion according to claim 1, wherein said preparation is administered in the form of an ointment.

4. The method of treating cervical erosion according to claim 1, wherein said preparation is administered in the form of a powder.

5. The method of treating cervical erosion according to claim 1, wherein said preparation is administered in the form of an injection solution.

* * * * *